United States Patent
Mattos et al.

(10) Patent No.: US 9,933,364 B2
(45) Date of Patent: Apr. 3, 2018

(54) PHASE SYNCHRONIZING PULSE AMPLITUDE MODULATION FLUOROMETER

(71) Applicants: Erico Rolim Mattos, Athens, GA (US); Mark Andreas Haidekker, Athens, GA (US); Ivan Kruglak, Boulder, CO (US)

(72) Inventors: Erico Rolim Mattos, Athens, GA (US); Mark Andreas Haidekker, Athens, GA (US); Ivan Kruglak, Boulder, CO (US)

(73) Assignee: Phytosynthetix LLC, Boulder, CO (US)

( * ) Notice: Subject to any disclaimer, the term of this patent is extended or adjusted under 35 U.S.C. 154(b) by 0 days.

(21) Appl. No.: 15/431,369

(22) Filed: Feb. 13, 2017

(65) Prior Publication Data

US 2017/0153181 A1    Jun. 1, 2017

Related U.S. Application Data

(62) Division of application No. 14/627,473, filed on Feb. 20, 2015, now Pat. No. 9,606,059.

(51) Int. Cl.
*G01N 21/64* (2006.01)
*G01N 21/63* (2006.01)

(52) U.S. Cl.
CPC ....... *G01N 21/645* (2013.01); *G01N 21/6486* (2013.01); *G01N 2021/635* (2013.01); *G01N 2201/061* (2013.01)

(58) Field of Classification Search
CPC .................................................. G01N 21/6486
See application file for complete search history.

(56) References Cited

U.S. PATENT DOCUMENTS

| 4,293,225 A * | 10/1981 | Wheaton | G01N 21/645 250/461.1 |
| 2009/0242797 A1 * | 10/2009 | Yazdanfar | A61B 1/00165 250/458.1 |
| 2015/0056645 A1 * | 2/2015 | Vacca | G01N 15/1459 435/29 |
| 2015/0177502 A1 * | 6/2015 | Matsukawa | G02B 21/0032 348/79 |

OTHER PUBLICATIONS

Schrieber et al., "PAM Fluorometry," Chlorophyll a Fluorescence: A Signature of Photosynthesis; Spring Science and Business Media, Eds. Papagergiou and Govindjee, Nov. 12, 2007, pp. 282-284. provided in parent U.S. Appl. No. 14/627,473.*

* cited by examiner

*Primary Examiner* — Yara B Green
(74) *Attorney, Agent, or Firm* — Douglas E McKinley

(57) ABSTRACT

A phase synchronizing pulse amplitude modulation fluorometer having an excitation light source capable of emitting a pulse of light that will induce fluorescence in an external object. A photo detector for detecting the pulse and a circuit to synchronize a pulse of light from the excitation light source with a pulse of light from an external light source.

10 Claims, 4 Drawing Sheets

PHASE SYNCHRONIZING PULSE AMPLITUDE MODULATION FLUOROMETER

CROSS REFERENCE TO RELATED APPLICATIONS

This application is a divisional application of, and claims priority to, U.S. application Ser. No. 14/627,473 filed Feb. 20, 2015, which is hereby incorporated by reference in its entirety.

TECHNICAL FIELD

This invention relates generally to improvements in fluorometers. Among other uses, the present invention may provide an improved fluorometer that may be used to measure chlorophyll fluorescence to investigate plant physiology, allowing the optimization of lighting provided to plants.

BACKGROUND OF THE INVENTION

Fluorometers have a wide variety of uses. By way of example, and not to limit the scope of the invention, fluorometers are used to measure chlorophyll fluorescence to investigate plant physiology and in the dairy industry to verify whether pasteurization has been successful.

In some fluorometry applications, there may be a light source that is pulsed. The fluorescence of an external object may vary depending on the application of the light source. For example, and not to limit the scope of the invention, the fluorescence of an external object may be strong when the light pulse is on, and less strong when the light pulse is off. As a further example, and not meant to limit the invention, when plants are grown with one or more electrically powered lights, it may be desirable to pulse the light source. In all applications using a pulsed light, it is useful to be able to measure and thereby understand the fluorescence at all phases of the pulsed light. Existing fluorometers do not have that capability. Among other advantages, and not meant to be limiting, the present invention provides that capability.

SUMMARY OF THE INVENTION

The present invention may include a phase synchronizing pulse amplitude modulation fluorometer, or PSPAMF. The PSPAMF of the present invention may include an excitation light source capable of inducing fluorescence in an external object, a fluorescence detector for detecting fluorescence in an external obj ect, and a circuit to synchronize a pulse of light from the excitation light source with a pulse of light from an external light source. The PSPAMF may include embodiments where the external light source is included as a part of the PSPAMF. In these embodiments, the circuit to synchronize the excitation light source with a pulse generated by the external light source may include an electronic connection between the external light source and the excitation light source. The electrical connection between the external light source and the excitation light source may be a wireless connection and it may be a wired connection.

The PSPAMF may include embodiments where the external light source is a part of the PSPAMF and where the circuit to synchronize the excitation light source with a pulse generated by the external light source makes use of an external reference. In such embodiments, the external light source and the excitation light source may both be configured to detect the external reference.

The PSPAMF may include embodiments where the external light source is not provided. Such embodiments may include a photo detector for detecting a pulse of light generated by the external light source. The photo detector may be in communication with the excitation light source, and may further be configured to cause the pulse of the excitation light source to correspond to one or more aspects of the pulse of the external light source. For example, and not meant to be limiting, the photo detector may be in communication with the excitation light source through a phase synchronizing circuit. In this manner, the pulse of the excitation light source may be configured to correspond to one or more of the rising edge, the zero crossing, the falling edge, the variable frequency, and the duty-cycle of the pulse generated by the external light source. The photo detector and the excitation light source may be in communication with a microprocessor. The microprocessor may further be configured to cause the excitation light source to produce a pulse that corresponds to one or more aspects of the pulse of the external light source. For example, and not meant to be limiting, the microprocessor may cause the excitation light source to produce a pulse that corresponds to one or more of the rising edge, the zero crossing, the falling edge, the variable frequency, and the duty-cycle of the pulse generated by the external light source.

As used herein, a fluorescence detector is any device that acts as an amplifying photodetector, including, without limitation, an avalanche photo diode (APD) and a photo multiplier tube (PMT).

The excitation light source may be any light source capable of generating a fluorescence response in the external object. For example, and not meant to be limiting, suitable light sources for the excitation light source of the PSPAMF include narrow band width emitting semiconductors; light emitting diodes; lasers; including a pulsed laser, a pumped laser, a diode-pumped solid-state laser, and a flashlamp pumped laser. Suitable light sources further include, but are not limited to, a pulsed arc-discharge lamp; a xenon flashlamp; a xenon flashlamp in combination with an excitation filter; a continuous-emmision lamp; a tungsten halogen lamp; and a tungsten halogen lamp with an opto-mechanical interrupter and an excitation filter.

While not meant to limiting, in embodiments where the excitation light source is a laser diode, the power of the laser diode may be between 5 mW and 200 mW.

While not meant to limiting, in embodiments where the PSPAMF is used to regulate light sources used for growing plants, the excitation light source may be a wavelength capable of promoting photosynthesis. In embodiments where the excitation light source is a wavelength capable of promoting photosynthesis, the excitation light source may or may not be powerful enough to promote photosynthesis.

While not meant to limiting, the excitation light source of the PSPAMF may be a directly focused laser, or a laser in communication with a fiber optic cable.

While not meant to limiting, the excitation light source of the PSPAMF may be configured to provide a saturation pulse. As used herein, a saturation pulse is an intense pulse of actinic light capable of momentarily saturating a plants photosynthetic system.

While not meant to limiting, the fluorescence detector of the PSPAMF may be an avalanche photo diode or a photo multiplier tube.

While not meant to limiting, the fluorescence detector of the PSPAMF may be an avalanche photo diode having an active area between 500 μm and 800 μm.

While not meant to limiting, the fluorescence detector of the PSPAMF may be an avalanche photo diode in communication with an optical long pass filter. The avalanche photo diode may further be mounted into a collimator tube, the collimator tube may further hold a lens, the lens may be aspherical, and the aspherical lens may be at an angle to a fiber optic cable or a direct focused laser.

While not meant to limiting, the fluorescence detector of the PSPAMF may be configured to measure the maximum fluorescence of the external object during saturation of the pulse.

While not meant to limiting, the photo detector of the PSPAMF may be configured to communicate at least one of the frequency, phase and duty-cycle of the pulse of the external light source to the phase synchronizing circuit.

While not meant to limiting, the phase synchronizing circuit may include a microprocessor While not meant to limiting, the photo detector of the PSPAMF may be wired to the circuit connecting the external light source with the phase synchronizing circuit, or a wireless circuit may connect the external light source with the phase synchronizing circuit.

While not meant to limiting, the photo detector of the PSPAMF may be configured to detect the intensity of the external light source. The photo detector of the the PSPAMF may be configured to detect at least one of the rising edge, the zero crossing, the falling edge, the variable frequency, and the duty-cycle of the pulse generated by an external light source.

While not meant to limiting, the phase synchronizing circuit of the PSPAMF may be configured to detect changes in the pulse generated by an external light source between 1 Hz and 1 MHz.

While not meant to limiting, the phase synchronizing circuit of the PSPAMF may be configured to detect changes in the pulse generated by an external light source between 0 and 100% duty-cycle.

While not meant to limiting, the phase synchronizing circuit of the PSPAMF may be configured to to adapt the excitation light to changes in the pulse generated by an external light source between 1 Hz and 1 MHz.

While not meant to limiting, the phase synchronizing circuit of the PSPAMF may be configured to adapt the excitation light to changes in the pulse generated by an external light source between 0 and 100% duty-cycle.

While not meant to limiting, the fluorescence detector of the PSPAMF may include operation in a single point mode wherein one or both of the excitation light and the fluorescence detector are directed toward a single location on the external object. For example, and not meant to be limiting, in a configuration where the PSPAMF is used to optimize the operation of an indoor plant growing operation, one or both of the excitation light and the fluorescence detector may be scanned on a representative spot in the vegetative matter, allowing the PSPAMF to survey the fluorescent response of that representative spot of the vegetative matter.

Conversely, and also not meant to be limiting, the fluorescence detector of the PSPAMF may include operation in a scanning mode wherein one or both of the excitation light and the fluorescence detector are directed toward multiple locations on the external object. For example, and not meant to be limiting, in a configuration where the PSPAMF is used to optimize the operation of an indoor plant growing operation, one or both of the excitation light and the fluorescence detector may be scanned across a large volume of vegetative matter in the growing area, allowing the PSPAMF to survey the fluorescent response across the entire volume of vegetative matter.

As a further example, and not meant to be limiting, the present invention may be operated in a greenhouse full of plants where it is desirable to measure the fluorescence across a broad area of the greenhouse. In such a configuration, the fluorescence detector may be a camera with a sensor having the capability to capture the image of a large portion of the plants within the greenhouse, or all of the plants within the greenhouse, onto the camera's sensor. In such a configuration, the excitation light may be a single, wide-arc flash of light across the plants in the greenhouse.

Alternatively, the fluorescence detector may be configured as a line array of sensors with the capability to acquire fluorescence emission along a straight line in the field of view. In such a configuration, the excitation light may be a single, wide-arc flash of light, with the sensor tilted to obtain the fluorescent response in a second dimension.

Yet another alternative is where the fluorescence detector is configured to read the overall fluorescence from a wide field of view. The excitation source in such an arrangement may be from a collimated source that sweeps the field of view, and the detected coordinates are obtained from the direction in which the source points.

As used herein, the term "circuit" means a path in which electrons from a voltage or current source flow. Such circuits may include one or more microprocessors, which would also fall within the applicant's use of the term "circuit" to describe an electrical path to synchronize a pulse of the excitation light source with a pulse of the external light source as used herein. The term circuit may further include an electrical path that synchronizes the excitation light source with a pulse of the external light source and the detection of fluorescence. The circuit used to synchronize a pulse of the excitation light source with a pulse of the external light source as used herein may thus be accomplished in a variety of ways, all of which may be referred to herein as a "phase synchronizing circuit."

For example, and not meant to be limiting, each of the external light source and the excitation light source may include a circuit to control one or more of the start, finish, duty cycle, duration, timing, frequency and intensity of a pulse of light generated by the external light source and the excitation light, respectively. The circuit may include a microprocessor programmed to provide each of these functions. Accordingly, a circuit may be provided in one or both the external light source and the excitation light source which may be configured to communicate directly with one and another by connecting the external light source and the excitation light source. This may be accomplished with a wired or a wireless connection. In this manner, by way of example and not meant to be limiting, the external light source may be configured to communicate one or more of the start, finish, duty cycle, duration, timing, frequency and intensity of a pulse of light generated by the external light source to the excitation light source. The excitation light source may then have a circuit configured to synchronize a pulse generated by the excitation light source with the pulse generated by the external light source, using the information communicated by the external light source.

Alternatively, the excitation light source may be configured to communicate one or more of the start, finish, duty cycle, duration, timing, frequency and intensity of a pulse of light generated by the excitation light source to the external light source. The external light source may then be configured to include a circuit that will synchronize a pulse generated by the external light source with the pulse generated by the excitation light source, using that communication.

In an analogous manner, the circuit to synchronize a pulse of the excitation light source with a pulse of the external light source can be accomplished by providing a photo detector that is capable of detecting a light pulse generated by the external light source. For example, and not meant to be limiting, the excitation light source may include a photo detector to detect one or more of the start, finish, duty cycle, duration, timing, frequency and intensity of a pulse of light generated by the external light source. Accordingly, the excitation light source may be configured to include a circuit connected to the photo detector to synchronize a pulse of light with a pulse of light generated by the external light source.

Alternatively, by way of example and not meant to be limiting, the excitation light source may be configured with a photo detector to detect one or more of the start, finish, duty cycle, duration, timing, frequency and intensity of a pulse of light generated by the external light source. The excitation light source may further include a circuit configured to synchronize a pulse generated by the excitation light source with the pulse generated by the external light source that was detected by the photo detector connected to the excitation light source. Such a circuit would also fall within the applicant's use of the term "circuit" when describing and claiming a circuit to synchronize a pulse of the excitation light source with a pulse of the external light source.

As used herein, the circuit to synchronize a pulse of the excitation light source with a pulse of the external light source may further make use of an external reference. As used herein, an "external reference" means any type of device, or a signal generated by such a device that can be detected by each of the external light source and the excitation light source. While not meant to be limiting, examples of a suitable external reference would include any device capable of sending a signal, such a Global Positioning System, or so-called GPS, and the signal produced by a GPS. A circuit connected to the external light source and a circuit connected to the excitation light source may then detect the signal from the external reference, and then generate a pulse of the external light source and a pulse of the excitation light source synchronized by timing one or more of the start, finish, duty cycle, duration, timing, frequency and intensity to one and another. Such circuits would also fall within the applicant's use of the term "circuit" to describe a "circuit" to synchronize a pulse of the excitation light source with a pulse of the external light source as used herein.

BRIEF DESCRIPTION OF THE DRAWINGS

The following detailed description of the embodiments of the invention will be more readily understood when taken in conjunction with the following drawings, wherein.

DETAILED DESCRIPTION OF EXEMPLARY EMBODIMENTS

Figure 1:
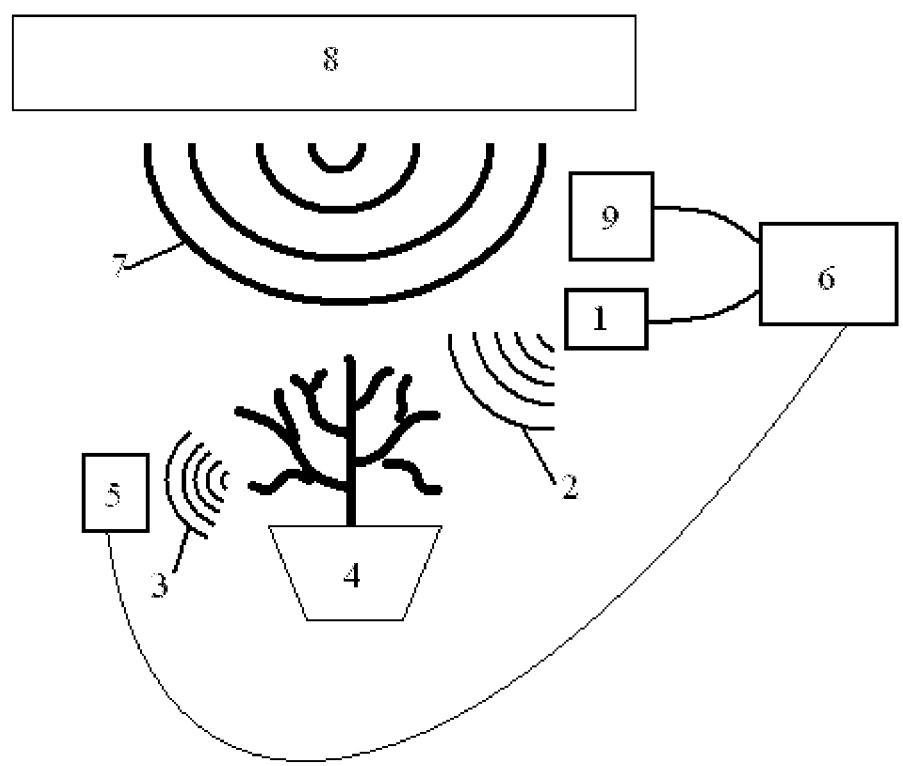
FIG. 1 is an illustration of one embodiment of the present invention.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

One exemplary embodiment of the present invention is shown in FIG. 1. As shown in FIG. 1, a phase synchronizing pulse amplitude modulation fluorometer has an excitation light source 1 capable of emitting light 2 that will induce fluorescence 3 in an external object 4. A fluorescence detector 5 for detecting fluorescence 2 in an external object 4 is also provided. The present invention may further include a photo detector 9 capable of detecting the pulse of light 7 from an external light source 8. The photo detector 9 may be connected to a circuit 6 which in turn may be connected to the excitation light source 1 that can synchronize a pulse of light 2 from the excitation light source 1 with a pulse of light 7 from an external light source 8. The circuit 6 may further be connected to the fluorescence detector 5.

Figure 2:
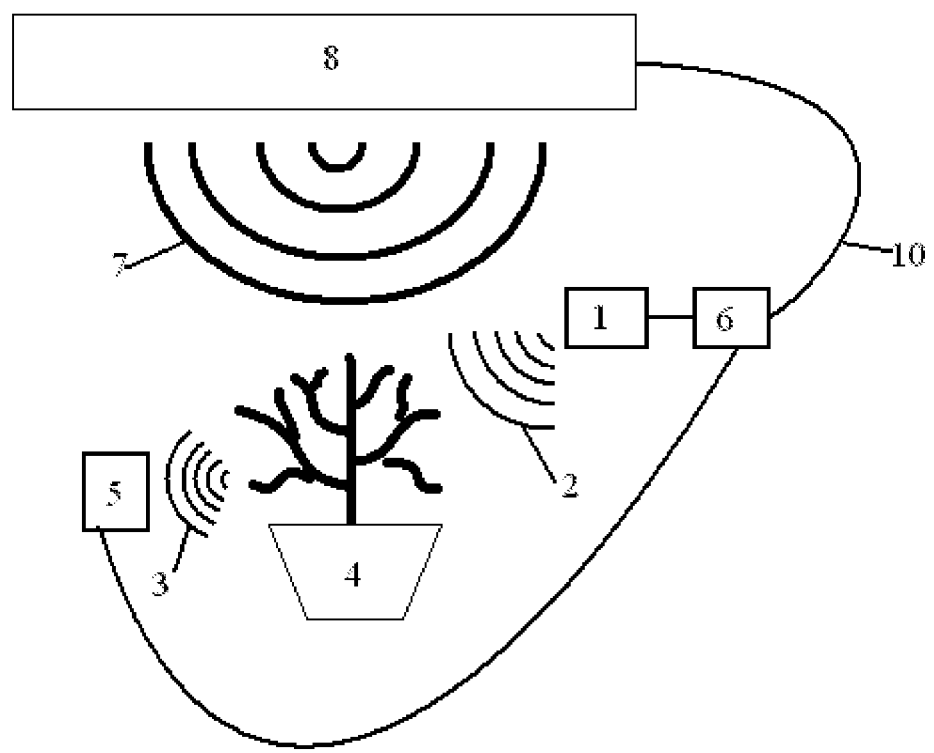
FIG. 2 is an illustration of one embodiment of the present invention where the excitation light source has a connection with the external light source.

As shown in FIG. 2, the phase synchronizing pulse amplitude modulation fluorometer (PSPAMF) may include embodiments where the external light source 8 is included as a part of the PSPAMF. In these embodiments, the circuit 6 to synchronize the excitation light source 1 with a pulse 7 generated by the external light source 8 may include an electronic connection 10 between the external light source 8 and the circuit 6. The electrical connection 10 between the external light source and the excitation light source may be a wireless connection and it may be a wired connection. The circuit 6 may further be connected to the fluorescence detector 5.

Figure 3:
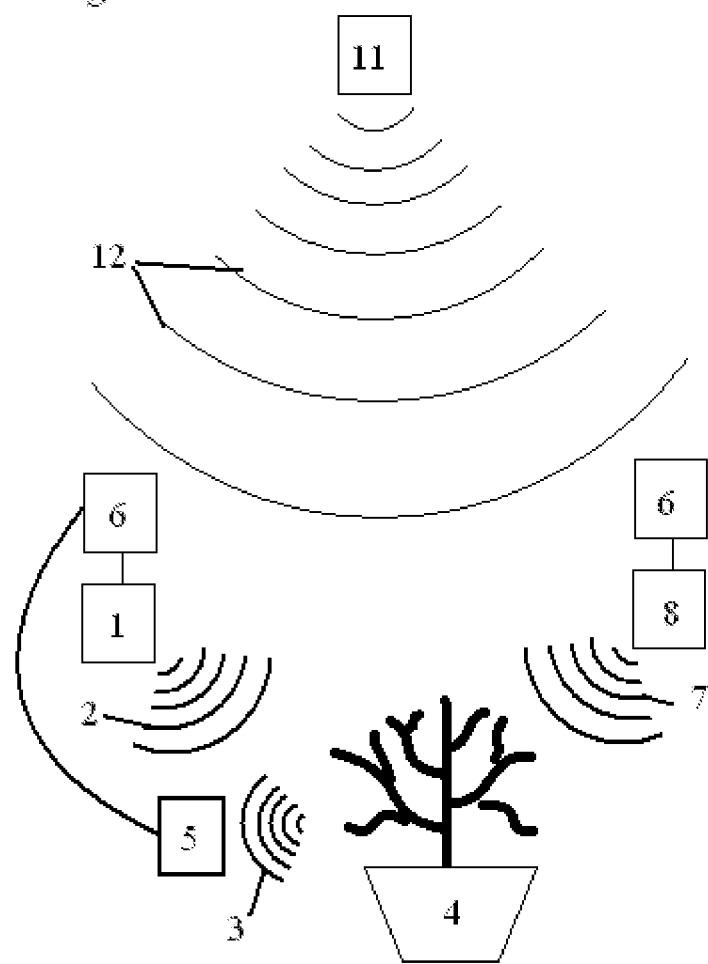
FIG. 3 is an illustration of one embodiment of the present invention utilizing an external reference.

As shown in FIG. 3, the PSPAMF may include embodiments where the external light source 8 is a part of the PSPAMF and where the circuit 6 to synchronize the excitation light source 1 with a pulse 7 generated by the external light source 8 makes use of an external reference 11. In such embodiments, the external light source 8 and the excitation light source 1 may both be configured to detect signals 12 sent by the external reference 10. The circuit 6 may further be connected to the fluorescence detector 5.

Figure 4:
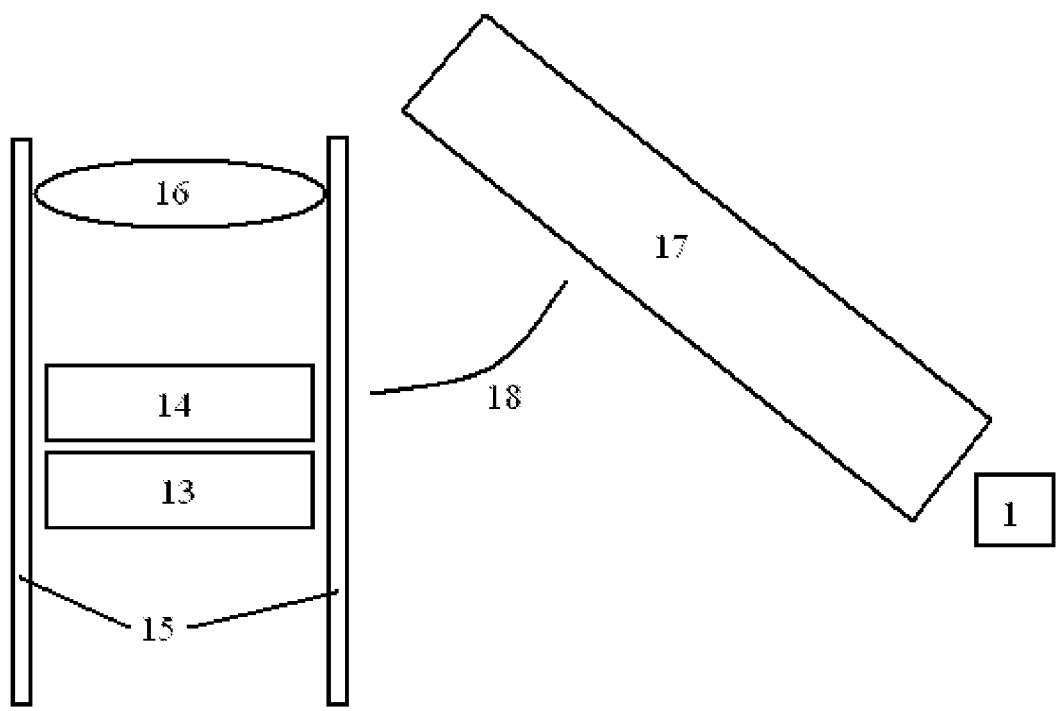
FIG. 4 is an illustration of one embodiment of the present invention showing the arrangement of an avalanche photo diode, optical long pass filter, lens, collimator tube, and fiber optic cable.

As shown in FIG. 4, the fluorescence detector of the PSPAMF may include an avalanche photo diode 13 in communication with an optical long pass filter 14. The avalanche photo diode 13 may further be mounted into a collimator tube 15. The collimator tube 15 may further hold a lens 16, and the lens may be aspherical. A fiber optic cable 17 may provide light 2 from the excitation light source 1, and may held at an angle 18 to the assembly of the avalanche photo diode 13, optical long pass filter 14, lens 16, and collimator tube 15.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

We claim:

1. A phase synchronizing pulse amplitude modulation fluorometer comprising, an excitation light source capable of inducing fluorescence in an external object; a fluorescence detector for detecting fluorescence in an external object, an external light source capable of generating a pulse of light, a photo detector for detecting a pulse of light generated by an external light source, and a circuit to synchronize a pulse of light from the excitation light source with a pulse of light from the external light source wherein the photo detector for detecting a pulse generated by an external light source is in communication with a phase synchronizing circuit and wherein the phase synchronizing circuit is configured to detect changes in the pulse between 1 Hz and 1 MHz.

2. The phase synchronizing pulse amplitude modulation fluorometer of claim 1 wherein the pulse of the external light source has a frequency, a phase and a duty-cycle and the photo detector for detecting a pulse generated by an external light source is configured to communicate at least one of the frequency, phase and duty-cycle of the pulse of the external light source to the phase synchronizing circuit.

3. The phase synchronizing pulse amplitude modulation fluorometer of claim 2 wherein a wired circuit connects the external light source with a phase synchronizing circuit and is configured to communicate at least one of the frequency, phase and duty-cycle of the pulse of the external light source to a phase synchronizing circuit.

4. The phase synchronizing pulse amplitude modulation fluorometer of claim 2 wherein a wireless circuit connects the external light source with a phase synchronizing circuit and is configured to communicate at least one of the frequency, phase and duty-cycle of the pulse of the external light source to the phase synchronizing circuit.

5. The phase synchronizing pulse amplitude modulation fluorometer of claim 2 wherein the photo detector is configured to detect the intensity of the external light source.

6. The phase synchronizing pulse amplitude modulation fluorometer of claim 2 wherein the pulse generated by the external light source has a rising edge, a zero crossing, a falling edge, a variable frequency, and a duty-cycle and the phase synchronizing circuit is configured to determine at least one of the rising edge, the zero crossing, the falling edge, the variable frequency, and the duty-cycle of the pulse generated by the external light source.

7. The phase synchronizing pulse amplitude modulation fluorometer of claim 2, wherein the phase synchronizing circuit is configured to detect changes in the pulse between 0 and 100% duty-cycle.

8. The phase synchronizing pulse amplitude modulation fluorometer of claim 2, wherein the phase synchronizing circuit is configured to adapt the excitation light to changes in the pulse between 1 Hz and 1 MHz.

9. The phase synchronizing pulse amplitude modulation fluorometer of claim 2, wherein the phase synchronizing circuit is configured to adapt the excitation light to changes in the pulse between 0 and 100% duty-cycle.

10. The phase synchronizing pulse amplitude modulation fluorometer of claim 1 wherein the photo detector for detecting a pulse generated by an external light source is a photodiode.

* * * * *